United States Patent [19]

Cabrera

[11] 4,445,391
[45] May 1, 1984

[54] LIQUID METERING AND TRANSFER VALVE ASSEMBLY

[75] Inventor: Pedro P. Cabrera, Miami, Fla.

[73] Assignee: Coulter Electronics, Inc., Hialeah, Fla.

[21] Appl. No.: 312,218

[22] Filed: Oct. 19, 1981

[51] Int. Cl.³ .............................................. B01L 3/02
[52] U.S. Cl. ................................. 73/864.12; 422/103
[58] Field of Search ........... 73/863.71, 863.72, 863.73, 73/864.81, 864.83, 864.84, 864.21, 61.1 C; 422/103

[56] References Cited

U.S. PATENT DOCUMENTS

| | | | |
|---|---|---|---|
| 3,583,232 | 6/1971 | Isreeli | 422/103 |
| 3,991,055 | 11/1976 | Godin | 73/864.84 |
| 4,152,391 | 5/1979 | Cabera | 73/864.83 |

Primary Examiner—S. Clement Swisher
Attorney, Agent, or Firm—Silverman, Cass & Singer, Ltd.

[57] ABSTRACT

A liquid transfer rotary valve assembly capable of measuring and delivering at least a pair of different sample volumes in the microliter range along with a predetermined volume of diluent as a pair of different dilutions directed to different locations. The valve assembly provided herein includes a pair of stationary outer disc members and a movable inner disc member sandwiched therebetween, the facing surface portions being sealingly frictionally engaged. Each disc has an axial central passage to accommodate a spindle. An external hollow loop is provided on one of the stationary discs having a precise volume in the microliter range. A segmenting passageway is provided on the movable inner disc member. A source of sample is communicatively coupled through the other stationary disc to the segmenting passage which is arranged in series with the external loop. After a continuous stream of sample is disposed through the serially connected segmenting passage and loop, the inner member is angularly moved to place the content of the segmenting passage in communication with a source of diluent and a passage leading exterior of the valve. Reverse angular movement of the valve element enables backwash through the valve subsequent to delivery.

14 Claims, 13 Drawing Figures

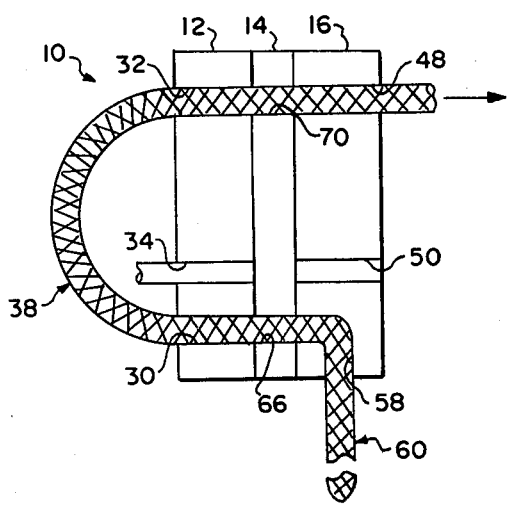
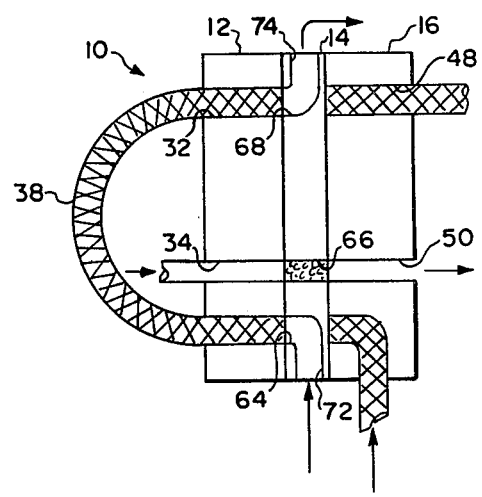
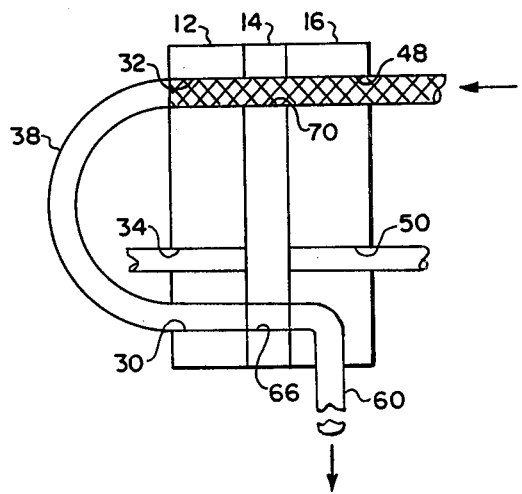

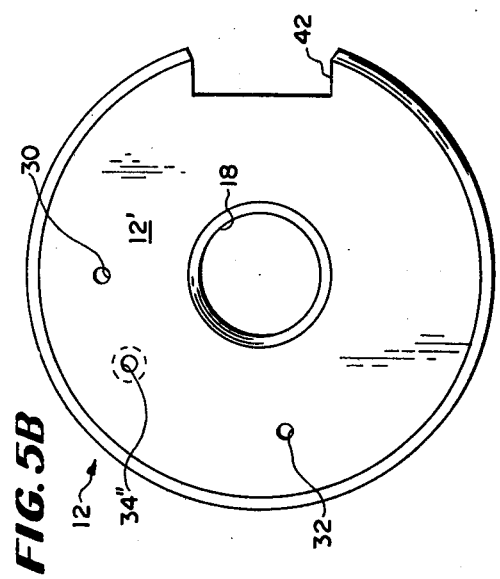
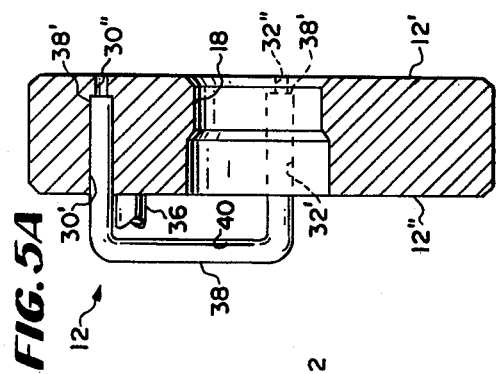
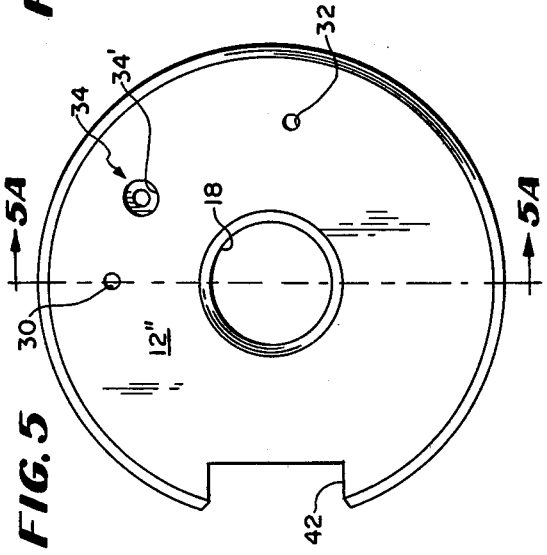
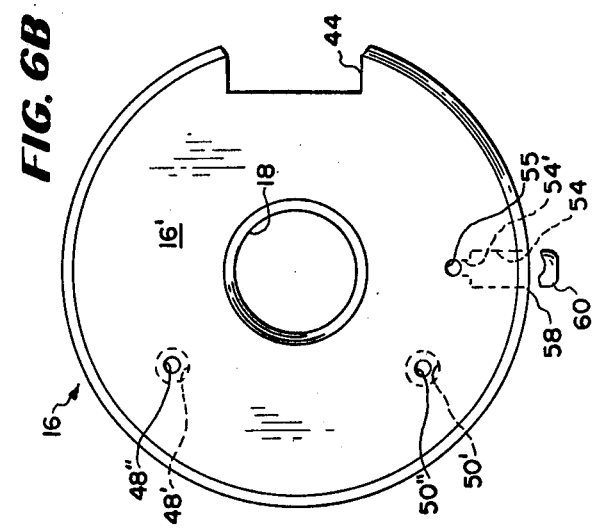
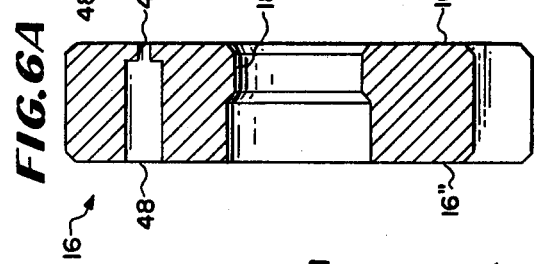
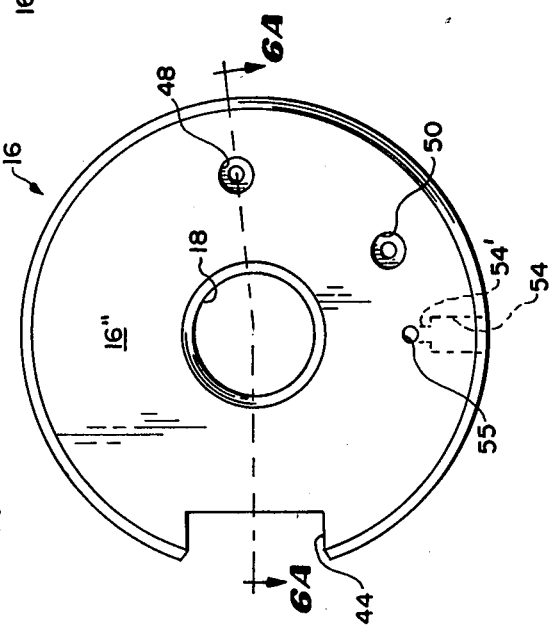

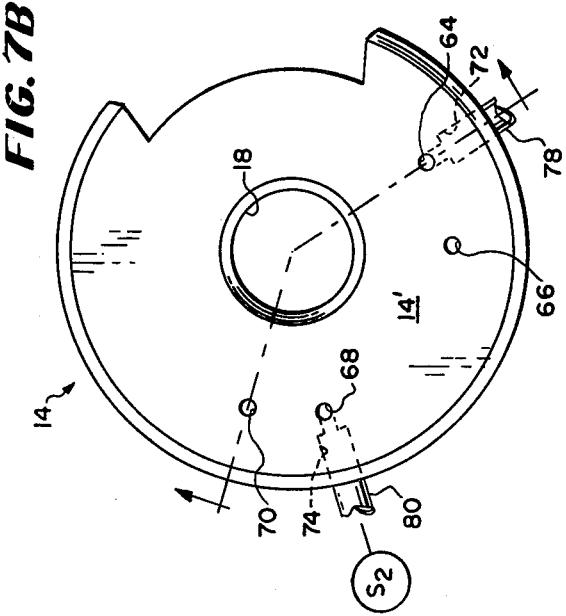
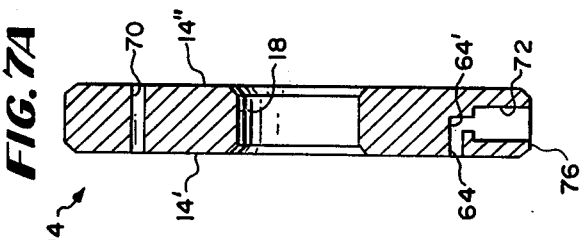
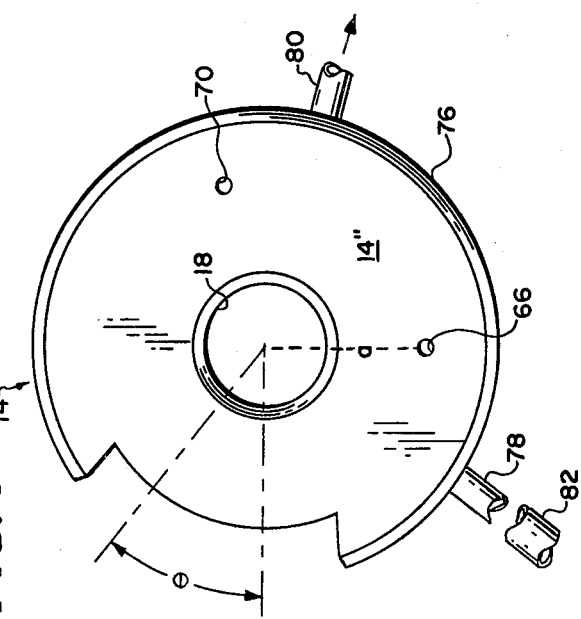

LIQUID METERING AND TRANSFER VALVE ASSEMBLY

CROSS REFERENCE TO RELATED PATENTS

This invention is an improvement over the liquid transfer valves of the type disclosed in applicant's U.S. Pat. No. 4,152,391 granted on May 1, 1979 and assigned to the Assignee of this application; said patent being hereby incorporated by reference into this application and made a part thereof for description of the background and functional operations of the diluting systems and valve assemblies therein disclosed.

Also hereby incorporated by reference herein and made a part hereof, are U.S. Pat. Nos. 3,567,390 and 3,991,055 granted respectively Mar. 2, 1971 and Nov. 9, 1976 and also owned by the Assignee of this application.

BACKGROUND OF THE INVENTION

This invention relates generally to liquid transfer systems, and more particularly provides a liquid transfer valve of the rotary operating type, such as disclosed in the referenced U.S. Pat. No. 4,152,391, for measuring and dispensing precise microliter volumes of samples, and which is characterized by the establishment of a pair of measuring chambers in a series coupled relationship capable of providing simultaneously a pair of precisely measured, different liquid volumes and directing each to a pair of different predetermined locations, each along with a respective same volume of diluent.

The liquid transfer valve provided in the referenced U.S. Pat. No. 4,152,391 included internal segmenting passageway means and at least one external hollow loop of precise internal volume thereby to provide the different volumetric quantities of a single liquid sample for dilution, each sample quantity being directed, along with a common volume of diluent, simultaneously to different predetermined locations. The segmenting passageway means were provided in the center movable disc of the patented valve, and the external loop was connected directly to said center disc. External connections for feed of diluent and for coupling to lines leading to the predetermined locations were made to the outer, stationary portions of the valve. This construction required relatively large volumes, especially for the external loop as its length required passage through one of the stationary valve members of the patented valve assembly and this gave rise to considerable so-called dead space whose volume was useless and contributed to considerable waste of sample. In addition to the relatively high cost of manufacture, the complexities of system operation required many connection couplings resulting in possible trouble areas resulting in wear and/or leakage. Considerable demand also has been encountered for conservation of sample volumes required for the testing procedure.

Conventionally, the patented valves as used commercially commonly included the feature thereof providing a second external loop, also coupled to the center movable disc, which loop functions as a measuring chamber when a prediluted sample was employed. Accordingly, not one but two external loops were required in the valve assembly to cover the possibility of using a prediluted sample, even if rarely encountered. Clearly this added to the cost. Where prediluted samples were encountered, a section of the transfer valve was not employed and in fact, was blocked off. Nevertheless, this section was required to be provided.

Sample volumes required to make the required dilutions were much higher than the minimums needed to make dilutions required by the technologically improved analytical apparatus now available. The quantities of samples obtained are limited and often are minimal, many times in the microliter range. Smaller volume sample dilutions were capable of being handled successfully. Nevertheless, the structures of the available valve assemblies, including the patented reference valves, sharply limited possible reduction in the actual sample volumes required in order to make dilutions for testing.

Thus a need has arisen to provide relatively small precisely measured volumes of liquid sample even in the microliter range, so as to minimize actual raw sampling volume requirements. Fulfillment of such need should be accomplished without increasing the complexity either of fabrication or operation of the transfer valve assembly. Accuracy is paramount. Capability of substitution of the resulting valve assembly for already installed prior valve assemblies, i.e. retro-fit, is an important factor which must be considered in providing for microliter sampling capability. One way of fulfilling the aforesaid need would be to reduce considerably the volume of dead space within any valve assembly employed, but there is considerable difficulty in effecting such reduction with presently available valve assemblies.

SUMMARY OF THE INVENTION

A rotary operating liquid metering and transfer valve for use in a diluting system, said valve including means defining a pair of measuring chambers arranged in series connection with a source of sample and themselves, one of said chambers constituting an external loop of precise interior volume and the other comprising a segmenting passageway, the loop coupled in series with the segmenting passageway for drawing of a continuous sample therethrough and means isolating each of said pair and respectively coupling each to a different source of diluent using the same volume and directing the measured sample volumes along with associated diluent to different preselected locations.

The valve assembly comprises a pair of stationary outer disc members and a rotary inner disc sandwiched therebetween and sealingly engaged with the interior faces of both outer discs. The hollow external loop is secured to one of the outer discs. The segmenting passageway is provided in the inner disc and constitutes the first measuring chamber. The loop secured to the outer disc constitutes the second measuring chamber.

The valve assembly operates between two conditions, load and delivery. An aspirator probe is coupled to the other of the stationary discs, directly or indirectly, and communicates to the serially connected chambers in one condition of the valve for drawing a continuous sampling through both measuring chambers. The valve operates to isolate the contents of each chamber and at the time, independently to couple said measuring chamber to diluent sources during the second delivery condition of the valve assembly for dispensing of said isolated volumes and the diluent associated therewith to desired locations. The valve assembly is returned to the first condition for backwashing the passageways and measuring chambers.

There is a marked reduction in dead space interior of the valve.

BRIEF DESCRIPTION OF THE DRAWINGS

FIG. 2 is a diagrammatic elevational view of the improved valve assembly illustrating the relationship thereof during the load or aspiration condition;

FIG. 3 is a diagrammatic elevational view of the improved valve assembly illustrating the relationship thereof during the delivery condition;

FIG. 4 is a diagrammatic elevational view of the improved valve assembly illustrating the relationship thereof during the backwash condition thereof securing subsequent to delivery;

FIGS. 5, 5A and 5B respectively illustrate the outer face, a side elevational sectional view taken along lines 5A—5A of FIG. 5 and an inner face view of one of the respective stationary members of the valve assembly according to the invention;

FIGS. 6, 6A and 6B respectively illustrate the outer face, a side elevational sectional view taken along lines 6A—6A of FIG. 6, and the inner face respectively of the other one of the stationary members of the valve assembly according to the invention, FIGS. 7, 7A and 7B respectively illustrate the one face, a side elevational sectional view taken along lines 7A—7A of FIG. 7, and the opposite face of the center inner movable member, respectively, of the valve assembly according to the invention.

DESCRIPTION OF PREFERRED EMBODIMENT

Figure 1:
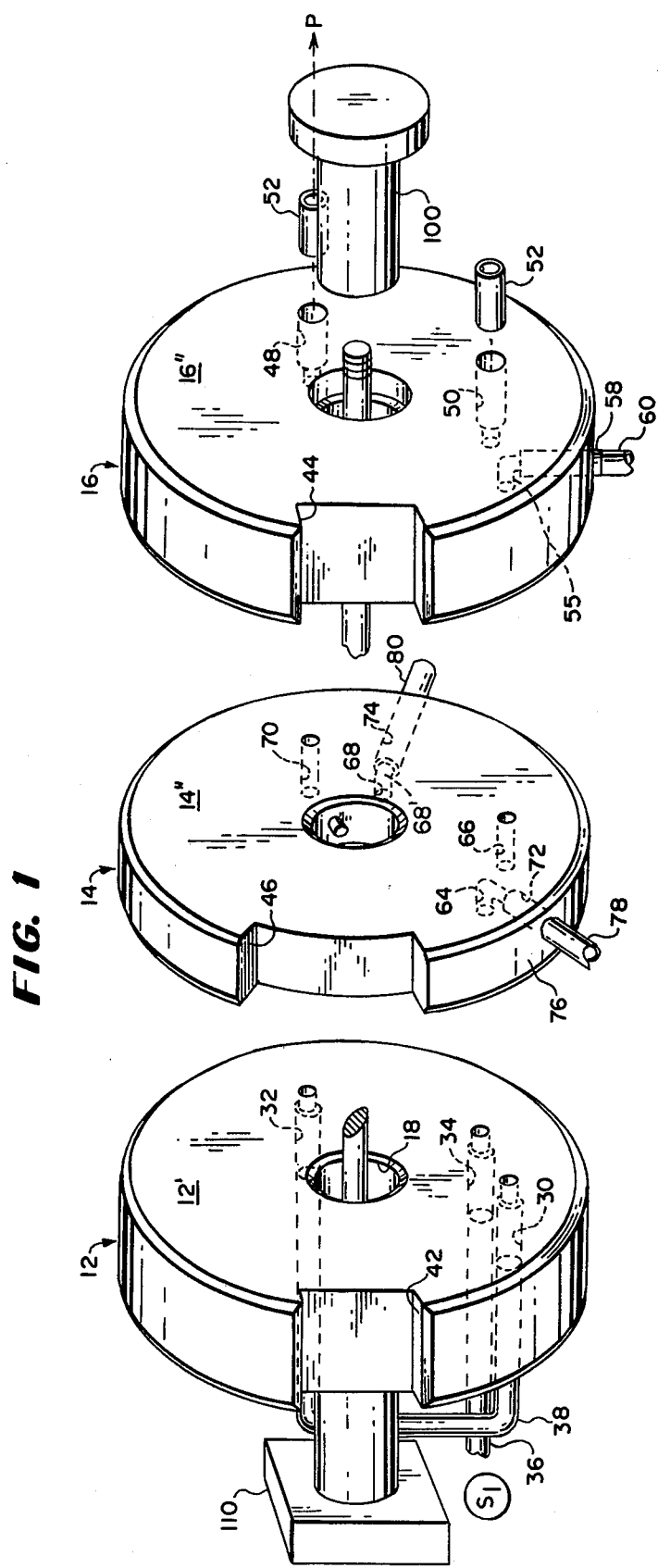
FIG. 1 is an exploded and diagrammatic representation of the liquid transfer valve assembly constructed in accordance with the invention herein.

The liquid transfer valve assembly according to the invention is capable of delivering from a single sample at least two different microliter segments, preferably simultaneously, for dilution with the same predetermined volume of diluent. Means are provided for establishing two sets of fluid paths, one set defining paths for traversal by a predetermined volume of diluent, the other set defining a series connection of a pair of precise measuring chambers of different volumes, one of which is provided by means defining a segmenting passageway formed in the inner or movable valve element and the other being provided by an external hollow loop secured fixedly to one of the stationary members. The external loop and the feeder passageways have precise internal dimensions, preferably holding a volume in the microliter range.

Briefly, the improved valve assembly is formed of a pair of members sealingly engaged sandwiched between an inner movable member. The valve assembly operates between a first condition during which sample is introduced from a source by way of an aspirator probe driven by an aspiration pump. The aspirator probe can be coupled directly, or through a conduit system, to a stationary portion of the valve. In the aspirating condition of the valve a continuous path is established between the aspirating probe via a segmenting passageway (constituting a first measuring chamber) and an external loop (constituting a second measuring chamber) through a connecting passageway, leading to the aspiration pump.

The valve assembly is operated to place same in the delivery condition, thereby placing the volume segmented from the continuous path by the segmenting passageway into a path established to direct diluent thereto for delivery from the valve to a selected location.

Simultaneously, the volume of sample contained in the second measuring chamber (namely the internal volume of the external loop) is coupled to a path through which diluent is introduced to sweep said volume of sample from the second measuring chamber for delivery to a second preselected location. Reference is made to U.S. Pat. No. 4,152,391 incorporated by reference herein for a description and illustration of the diluting and testing system into which the valve according to the invention is well adapted for placement. With the valve according to the invention, the predilution cycle is omitted with no provision required to be established therefor.

The valve assembly constructed in accordance with the invention herein comprises an assembly 10 formed of a pair of coaxially arranged outer stationary disc elements 12 and 16 having a rotatably movable central valve disc element 14 sandwiched therebetween. The stationary elements 12 and 16 are arranged apart only sufficiently to accommodate the thinner central element therebetween.

The outer elements 12 and 16 are provided with inner faces 12' and 16' which are engaged sealingly with faces 14' and 14" of the inner element 14. Element 12 also has an outer face 12" and element 16 has outer face 16". Faces 12', 14', 14" and 16' are machined carefully, stress relieved as by heat treatment and coated with an acid resistant chromium oxide-aluminum coating whereby wear is reduced; friction and binding also are reduced.

Each of the valve disc elements 12, 14 and 16 have a central passageway 18 of the same inner diameter, and all are mounted coaxially on a spindle 20 including support elements 22 and 24 and shaft 26. The mounting is described in U.S. Pat. No. 4,152,391 and reference is made thereto for the description.

In FIG. 1, the left hand element 12 carries the external hollow loop while the right hand element 16 carries either the aspirator probe directly coupled thereto or has said probe adapted to be coupled thereto by way of a conduit coupling.

A pair of axially parallel through passageways 30 and 32 are formed in stationary disc element 12. Another through passageway 34 is formed in disc element 12 parallel axially to the passageways 30 and 32 but angularly spaced therefrom so that a radial line taken through the axial center of passageway 34 defines a precise angle $\theta$ with a radial line taken through the axial center of passageway 30. The passageway 34 includes a short portion 34" of small diameter opening to the inner face 12' while the larger diameter portion 34' opens to the outer face 12" for receiving nipple 36 for coupling to a source of diluent.

The axial centers of passageways 30, 32 and 34 are spaced identically a radial distance "a" from the center axis of the disc 12. Passageways 30 and 32 each have a major portion 30' and 32' of large diameter compared to the short portions 30" and 32", each of which opens to the inner face 12'. The larger diameter portions 30' and 32' open to the outer face 12" of element 12. Passageway portions 34", 30" and 32" have the same inner diameter.

An external hollow loop 38 is secured to the element 12 with opposite ends 38' seated tightly fully in the larger diameter passageway portions 30' and 32'. The external loop 38 has a precise internal volume. The inner diameter of the hollow loop 38 preferably is uniform with the opposite ends 38' having an inner diameter equal to the diameter of the smaller passageway portions 30″ and 32′ of passageways 30 and 32. The ends 38′ are inserted fully within passageway portions 30′ and 32′ to abut the inner ends of passageway portions 30′ and 32′. Thus a precise volume of liquid can be contained within the measuring chamber 40 defined within the hollow external loop.

The stationary valve elements 12 and 16 are provided with circumferential notches 42 and 44 while center valve element 14 is provided with a notch 46 of the same depth but encompassing a greater angular distance along the circumferential opening length than the angular extent of notches 42 and 44. Notches 42 and 44 are aligned with the opposite sides of said notches limiting the relative angular rotation of the center valve element 14 to an angular distance equal to the difference between the length of notches 42, 44 and the length of notch 46. The angular rotation of the center valve element 16 required to change the valve assembly 10 from one condition to its other condition is represented by angle $\theta$.

When the valve elements 12, 14 and 16 are assembled to constitute the valve assembly 10, all of the axially directed passageways and portions thereof which communicate with other passageways carried by the valve elements are coaxial, and all are parallel to the common center axis of said elements 12, 14 and 16.

The mounting of the valve elements 12, 14 and 16 on spindle 100 is the same as described in respect of the valve disc elements disclosed in referenced U.S. Pat. No. 4,152,391 and reference is made thereto for a description of such mounting.

A pair of like axially parallel passageways 48 and 50 are formed in the other stationary valve element 16, each passageway 48 and 50 having a larger diameter long portion 48′ and 50′ opening to the outer face 16″ of element 16 with smaller diameter short portion 48″ and 50″ opening to the inner face 16′ of element 16. A cylindrical nipple 52 is tightly seated within each of the large portions 48′ and 50′ extending outward of element 16 and opening to the exterior of the valve for coupling to the aspirator pump P and to suitable conduit means leading to one of the preselected delivery locations, here to the location intended to receive the smaller segmented volume of sample, as will be described.

The stationary valve element 16 also is provided with a radial bore 54 opening to the outer circumferential surface of the element 16. The inner end 54′ of bore 54 communicates with a short axial bore 55 formed parallel to the axis of the valve element 16 and opening to the inner face 16′ thereof. Thus bores 54 and 56 together constitute an angular passageway 58. The aspirator probe 60 is adapted to be coupled directly to the bore 54 by a conduit, or directly received within bore 54, said bore 54 being of the same inner diameter as passageway portions 30′ and 32′ and passageway portions 48′ and 50′ receiving tightly therein, either a nipple 62 or the aspirator probe 60 itself.

The rotatably movable center valve disc element 14 is provided with two pair of passageways, first pair 64,66 and second pair 68,70. Passageways 66 and 70 are formed as through passageways of precise uniform inner diameter while passageways 64 and 68 extend in an axial direction only partially through the valve element 14 from face 14′ of said element. A pair of radial bores 72 and 74 are provided in element 14 entering from the outer circumferential surface 76 threof and communicating to the inner end 64′ and 68′ of partial passageways 64 and 68. The inner diameter of bores 72 and 74 is sufficient (the same as the inner diameters of the larger portions of bores 54 and 56, for example), to enable seating therein of nipples 78 and 80, one of which (78) is capable of being coupled to a conduit 82 leading to the preselected delivery location for receiving the larger volume of sample which comprises the interior volume of the hollow loop 38 and the other (80) enabling coupling thereto of a conduit 84 leading from a source $S_2$ of diluent for directing the predetermined volume of diluent to the hollow loop 38 when the valve element 14 is rotated to place the valve 10 in its delivery condition from its load condition.

When the valve element 14 is rotated from its load condition to the delivery condition, the through segmenting passageway which defines the smaller measuring chamber is brought into communication with the passageways enabling a predetermined volume of diluent, i.e. equal to the same volume as directed through the hollow loop 38, introduced via passageway 34 to drive the content of the segmenting passageway to the predetermined location via passageway of valve element 16.

As will be observed, the amount of dead space is minimized within the valve assembly 10 as constructed in accordance with the herein invention. Such dead space as remains constitutes only the volume within passageway of the center valve disc 14 and that quantity or volume of sample contained in angular passageway 58 of valve element 16 and in nipple 52 and the conduit leading from nipple 52 to the aspirator pump P. This is minimal compared to prior structures. When delivery is completed simultaneously to the different preselected delivery locations where examination of the respective diluted samples occur, the valve element 14 again is rotated but in the reverse direction to return the valve assembly 10 to its aspiration condition, as illustrated in FIG. 4. At this time, either the aspiration pump P is reversed to feed diluent to the valve 10 or an alternate connection made between a source of diluent and passageway 48 of valve element 16. Diluent is pumped, as from a source thereof, along the same route traversed previously by the sample, i.e. through nipple 52 and passageway 48, through the segmenting passageway 66, the angular passageway 58, through the interior of hollow loop 38, through segmenting passageway 70, then through the angular passageway 58 and traversing the interior of the aspirator probe 60 to a discharge location.

The internal volume within the external loop 38 is selected to be in the microliter range as compared with the milliliter range necessitated by the construction of the patented reference transfer valve assembly. This results in considerable conservation of sample volume required to be obtained.

It is believed apparent that much variation and substitution of equivalents are capable of being made without in any way departing from the spirit and scope of the invention as defined in the appended claims.

What I claim is:

1. A liquid metering and transfer valve assembly for use in a diluting system for providing at least a pair of segmented precise samples from a single liquid sample source, the volume of one segmented sample being different than the volume of the other segmented sample of said pair, said valve assembly being operable between a load and a delivery condition and comprising means defining a first and second segmenting portion in series communication for receiving a continuous volume of sample from said source, means for isolating the contents of said first and second segmenting portions one from the other and means for combining each of said first and second isolated contents with a precise volume of diluent and delivering said isolated contents with their associated amount of diluent to respectively different preselected exterior locations, said first segmenting portion comprising internal segmenting passageway means having a precise internal volume and said second segmenting portion comprising an external hollow loop having a precise internal volume different from the volume of the segmenting passageway means.

2. The valve assembly as claimed in claim 1 in which said metering and transfer valve assembly is formed of a pair of spaced outer stationary valve elements and an inner movable valve element sandwiched between said outer valve elements, said inner valve element having opposite faces sealingly frictionally engaged with adjacent faces of said outer valve elements, said inner valve element carrying said first segmenting portion and a second segmenting passageway, one of said outer valve elements carrying said external loop, said inner valve element arranged in the load condition of the valve whereat said first segmenting portion is in communication with one end of said external hollow loop and said second segmenting passageway is in communication with the opposite end of said external hollow loop, said inner valve element being movable angularly to segment the volume of sample within said first portion isolating same from said continuous volume and place same in the path taken by the predetermined amount of diluent from said diluent source for delivery to one preselected location, said angular movement isolating the volume within the external hollow loop and placing same in communication with a diluent source for directing said isolated volume together with the same amount of diluent to the exterior of said valve assembly for delivery to the other preselected location.

3. The valve assembly as claimed in claim 1 or claim 2 in which said inner valve element is provided with a pair of angular passageways leading from the exterior of said inner element to communicate with the external loop in the delivery condition of the valve assembly.

4. The valve assembly as claimed in claim 1 or 2 in which said external loop and said segmenting portions are in series communication.

5. The valve assembly as claimed in claims 1 or 2 in which said external loop and said segmenting passageways are in continuous series communication.

6. The valve assembly as claimed in claim 2 in which said source of sample is coupled to said valve assembly by way of an aspirator probe element coupled directly to the other one of said stationary valve elements.

7. The valve assembly as claimed in claim 2 in which said other one of said stationary elements is coupled to the source of sample and sample is introduced to said valve assembly by way of said other stationary valve element.

8. The transfer valve assembly as claimed in claim 2 in which there is an angular passageway formed in the other of said stationary valve elements leading from the outer circumferential surface thereof to the inner face thereof, the said angular passageway communicating between the source of sample and the said first segmenting portion in the loading condition of the valve assembly.

9. The transfer valve assembly as claimed in claim 2 in which there is an angular passageway formed in the other of said stationary valve elements leading from the outer circumferential surface thereof to the inner face thereof, the said angular passageway communicating between the source of sample and the said first segmenting portion in the loading condition of the valve assembly and there is a hollow probe element connected directly to said other of said stationary valve elements at the entrance of said angular passageway, said probe element capable of communicating with a sample source.

10. A liquid rotary metering and transfer valve assembly for use in a diluting system for providing at least a pair of segmented precise samples from a single liquid sample source, the volume of one segmented sample being different than the volume of the other segmented sample of said pair, said valve assembly being operable between a load and a delivery condition, said valve assembly comprising passage means defining first and second segmenting portions in series communication for receiving a continuous volume of sample from said source, means isolating the contents of said first and second segmenting portions one from the other, means for combining each of said first and second isolated contents with a precise volume of diluent from a source of diluent, means for delivering said isolated contents to different preselected exterior locations, said first segmenting portion having a precise internal volume and said second segmenting portion comprising an external hollow loop having a precise internal volume different from the volume of the segmenting passageway.

11. The valve assembly as claimed in claim 10 in which said metering and transfer valve assembly includes at least one stationary valve element and at least one movable valve element in face to face sealingly frictional engagement and one of said elements carrying said first segmenting portion, a second segmenting passageway and one of said stationary and movable valve elements carrying said external loop.

12. The valve assembly as claimed in claim 10 in which said movable valve element being arranged in the load condition of the valve with said first segmenting portion in communication with one end of said external hollow loop and said second segmenting passageway in communication with the opposite end of said external hollow loop, said movable valve element operable to segment the volume of sample within said first portion isolating same from said continuous volume and placing same in the path taken by the predetermined amount of diluent from said diluent source for delivery to one preselected location, the said movement also isolating the volume within the external hollow loop and placing same in communication with a diluent source for directing said isolated volume together with the same amount of diluent to the exterior of said valve assembly for delivery.

13. The valve assembly as claimed in claim 10 in which the source of sample is coupled to said valve assembly by way of an aspirator probe coupled directly to one of the valve elements.

14. The valve assembly as claimed in claim 11 in which the source of sample is coupled to said valve assembly by way of an aspirator probe coupled directly to one of the valve elements.

* * * * *